United States Patent [19]

Gardner

[11] 4,113,869

[45] Sep. 12, 1978

[54] TETRAHYDROISOQUINOLINE BASIC ETHERS AND PHARMACEUTICAL COMPOSITIONS AND METHODS EMPLOYING THEM

[75] Inventor: Derek Victor Gardner, Bishop Stortford, England

[73] Assignee: Beecham Group Limited, United Kingdom

[21] Appl. No.: 710,446

[22] Filed: Aug. 2, 1976

[30] Foreign Application Priority Data

Aug. 9, 1975 [GB] United Kingdom ............. 33283/75

[51] Int. Cl.² ................. C07D 217/16; A61K 31/47
[52] U.S. Cl. ............................ 424/258; 260/287 D; 260/288 D; 260/283 SA; 260/289 D
[58] Field of Search ........ 260/288 D, 287 D, 283 SA, 260/289 D, 247.5 GP; 424/258, 248.56

[56] References Cited

U.S. PATENT DOCUMENTS

| | | | |
|---|---|---|---|
| 3,479,358 | 11/1969 | Hansen et al. ................... | 260/286 |
| 3,666,763 | 5/1972 | Grethe et al. ................... | 260/289 R |
| 3,855,227 | 12/1974 | Hollander et al. .............. | 260/286 R |
| 3,870,722 | 3/1975 | Houlihan et al. ............... | 260/283 R |
| 3,872,125 | 3/1975 | Houlihan et al. ............... | 260/283 R |
| 3,878,215 | 4/1975 | Houlihan et al. ............... | 260/283 R |
| 3,910,924 | 10/1975 | Tamura et al. .................. | 260/288 R |
| 3,947,456 | 3/1976 | Rheiner ............................ | 260/289 R |
| 3,953,456 | 4/1976 | Nakagawa et al. ............. | 260/288 R |
| 4,013,663 | 3/1977 | Westermann et al. ......... | 260/287 D |

*Primary Examiner*—Donald G. Daus
*Assistant Examiner*—Diana G. Rivers
*Attorney, Agent, or Firm*—Jacobs & Jacobs

[57] ABSTRACT

Compounds of the formula (II):

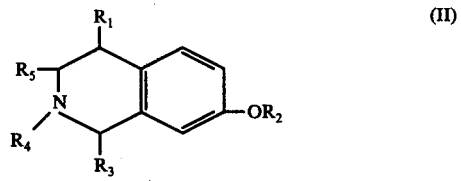

(II)

and salts thereof wherein $R_1$ is a $C_{1-6}$ alkyl, $C_{3-6}$ cycloalkyl phenyl, naphthyl, aralkyl, substituted phenyl or substituted naphthyl group; $R_2$ is a group:

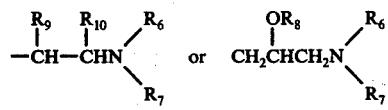

wherein $R_6$ is a hydrogen atom or a $C_{1-6}$ alkyl group, $R_7$ is a hydrogen atom or a $C_{1-6}$ alkyl, phenyl, tolyl, or benzyl group or $R_6$ is linked to $R_7$ so that the $NR_6R_7$ moiety is a 5-,6- or 7- membered ring, $R_8$ is a hydrogen atom or a $C_{1-4}$ alkyl group or is joined to $R_6$ to form part of a morpholino ring and $R_9$ and $R_{10}$ are each hydrogen atoms or $C_{1-4}$ alkyl groups; $R_3$ is a hydrogen atom or a $C_{1-6}$ alkyl or a trifluoromethyl group; $R_4$ is a hydrogen atom or a $C_{1-6}$ alkyl, benzyl or phenyl group or an acyl group containing from 2 to 7 carbon atoms and $R_5$ is a hydrogen atom or a $-C_{1-6}$ alkyl group; have been found to be mood modifying agents and anorexia agents.

33 Claims, No Drawings

TETRAHYDROISOQUINOLINE BASIC ETHERS AND PHARMACEUTICAL COMPOSITIONS AND METHODS EMPLOYING THEM

The present invention relates to novel compounds, to their preparation and to pharmaceutical compositions containing them.

British patent specification No. 1,335,261 discloses inter alia that the compounds of the formula (I):

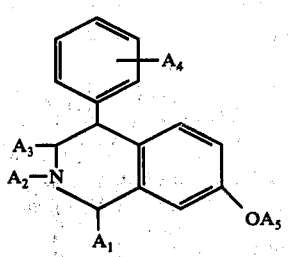

wherein $A_1$ is hydrogen or a $C_{1-4}$ alkyl group, $A_2$ is a $C_{1-4}$ alkyl or phenyl group, $A_3$ is a hydrogen atom $A_4$ is a halogen atom or a nitro, amino or substituted amino group and $A_5$ is a hydrogen atom or $C_{1-4}$ alkyl group possess antidepressant activity. U.S. Pat. No. 3,870,722 discloses inter alia that the compounds of the formula (I) wherein $A_1$ is a hydrogen atom, $A_2$ is a methyl group, $A_3$ is a $C_{4-8}$ alkyl group, $A_4$ is a hydrogen atom and $A_5$ is a lower alkyl group possess hypolipidaemic activity.

It has now been found that compounds of the formula (I) can serve as intermediates in the preparation of novel basic ethers which possess anorexic inducing and mood modifying activity. The present invention provides compounds of the formula (II):

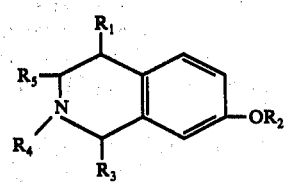

and salts thereof wherein $R_1$ is a $C_{1-6}$ alkyl, $C_{3-6}$ cycloalkyl phenyl, naphthyl, aralkyl, substituted phenyl or substituted naphthyl group; $R_2$ is a group:

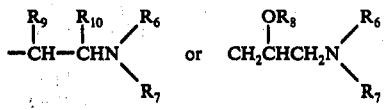

wherein $R_6$ is a hydrogen atom or a $C_{1-6}$ alkyl group, $R_7$ is a hydrogen atom or a $C_{1-6}$ alkyl, phenyl, tolyl, or benzyl group or $R_6$ is linked to $R_7$ so that the $NR_6R_7$ moiety is a 5-, 6- or 7-membered ring, $R_8$ is a hydrogen atom or a $C_{1-4}$ alkyl group or is joined to $R_6$ to form part of a morpholino ring and $R_9$ and $R_{10}$ are each hydrogen atoms or $C_{1-4}$ alkyl groups; $R_3$ is a hydrogen atom or a $C_{1-6}$ alkyl or a trifluoromethyl group; $R_4$ is a hydrogen atom or a $C_{1-6}$ alkyl, benzyl or phenyl group or an acyl group containing from 2 to 7 carbon atoms and $R_5$ is hydrogen atom or a $C_{1-6}$ alkyl group.

By the term "substituted phenyl or naphthyl group" is meant a phenyl or naphthyl group substituted by one or two halogen atoms or trifluoromethyl, $C_{1-4}$ alkyl, hydroxy, $C_{1-4}$ alkoxy, nitro, amino, methylamino, dimethylamino, diethylamino, carboxy, methoxycarbonyl, ethoxycarbonyl, cyano, carboxamido, sulphonamido, trifluoromethoxy or trifluoromethylthio groups or by an acyl group containing up to 7 carbon atoms.

By the term "aralkyl group" is meant a benzyl or benzhydryl group or a benzyl or benzhydryl group substituted by one or two halogen atoms or trifluoromethyl, $C_{1-4}$ alkyl, hydroxy, $C_{1-4}$ alkoxy, nitro, amino or cyano groups.

Suitably $R_1$ is a phenyl or naphthyl group or a phenyl group substituted by a fluorine, chlorine or bromine atom or a methyl, methoxy or trifluoromethyl group.

Suitably $R_2$ is a group:

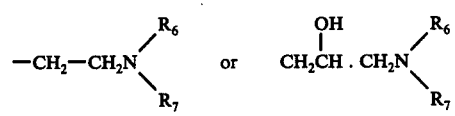

wherein $R_6$ and $R_7$ are as defined in relation to formula (II)

Suitably $R_6$ is a hydrogen atom or a methyl group

Suitably $R_7$ is a hydrogen atom or a methyl, ethyl or benzyl group.

Most suitably $R_3$ is a hydrogen atom or a methyl group.

Preferably $R_3$ is a hydrogen atom.

Most suitably $R_4$ is a hydrogen atom or a $C_{1-4}$ alkyl or benzyl group.

Preferably $R_4$ is a methyl group.

Most suitably $R_5$ is a hydrogen atom or $C_{1-4}$ alkyl group

Preferably $R_5$ is a hydrogen atom.

Particularly suitable values of $R_2$ include those of the sub-formulae (a) - (d):

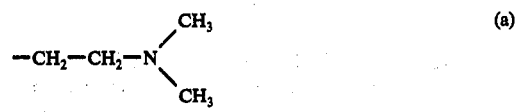 (a)

 (b)

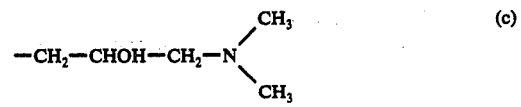 (c)

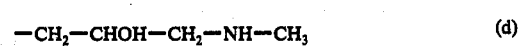 (d)

Particularly suitable compounds of the formula (II) include those of the formulae (III), (IV), (V) and (VI):

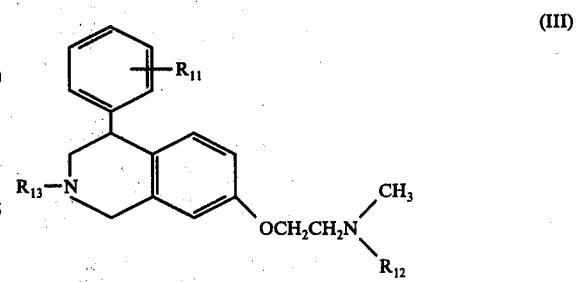 (III)

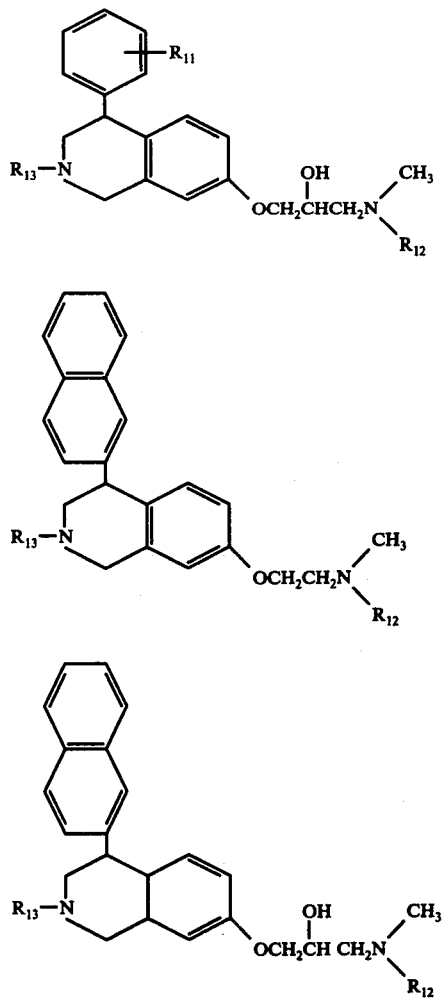

and salts thereof wherein $R_{11}$ is a hydrogen, fluorine or chlorine atom or a nitro, trifluoromethyl, methyl or methoxy group and $R_{12}$ and $R_{13}$ are each a hydrogen atom or a methyl or ethyl group.

Suitably $R_{11}$ is a hydrogen, fluorine or chlorine atom or a trifluoromethyl group.

Preferred compounds for inducing anorexia include those wherein $R_{11}$ is a 4 — fluorine or 4 — chlorine atom or a 4 — trifluoromethyl group.

Preferred compounds useful in the treatment of depression include those wherein $R_{11}$ is a 3 — trifluoromethyl group.

Suitably $R_{12}$ is a hydrogen atom or a methyl group.
Preferably $R_{12}$ is a methyl group.
Suitably $R_{13}$ is a methyl or ethyl group.
Preferably $R_{13}$ is a methyl group.

The compounds of the formula (II) exist as a number of stereoisomers. Accordingly the present invention provides the compounds of the formula (II) as pure stereoisomers as well as mixtures of these stereoisomers.

Since the compounds of this invention are nitrogenous bases they are able to form acid addition salts in conventional manner. Normally, such salts are those formed from pharmaceutically acceptable organic or inorganic acids such as citric, acetic, propionic, lactic, tartaric, mandelic, succinic, oleic, glutaric, gluconic, methanesulphonic, toluenesulphonic, sulphuric, phosphoric, hydrobromic or hydrochloric acid.

Compounds within the formula (II) affect the central nervous system. Thus depending on the dosage used, certain compounds of the formula (II) are able to produce anorexic or mood modifying effects in mammals.

Accordingly in one of its aspects the present invention provides pharmaceutical compositions which comprise a compound of this invention as hereinbefore described together with a pharmaceutically acceptable carrier.

Normally, the compositions of this invention are adapted for oral administration to humans although compositions adapted for parenteral administration are also envisaged.

The most suitable dosage forms are unit dosage forms such as tablets, capsules, sachets and the like which contain a predetermined quantity of active material.

Such unit dosage forms normally contain from 0.05 to 200 mg. and preferably from 0.5 mg. to 100 mg. of active material and may be taken once a day or several times a day according to the dose desired. Generally a human adult will be administered from 0.5 to 500 mgs. per day.

If the composition of this invention is intended for the induction of anorexia the composition will normally be in the form of a solid unit dosage form which contains from 0.5 mg. to 200 mg. of active ingredient, for example 1 mg. to 100 mg. of active ingredient.

If the composition of this invention is intended for mood-modification such as anti-depressant effects, it is likely that it will be used as a solid unit dosage form which contains from 0.05 to 50 mg. of active ingredient, for example 1 mg. to 25 mg. of active ingredient.

In a further aspect this invention provides a method of suppressing appetite, which comprises administering an anorexically effective amount of a compound of this invention.

In a further aspect this invention provides a method of reducing depression which comprises administering an antidepressively effective amount of a compound of this invention.

The useful anorexic activity of compounds of this invention may be determined by the oral administration to hungry rats of the compound and measuring the reduction in their food intake. The results given in Table 1 were obtained for compounds of the formula (VII):

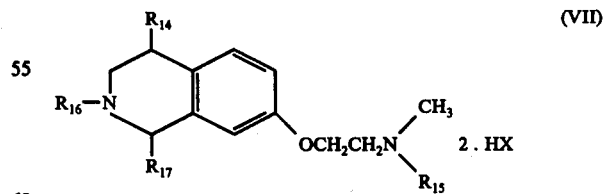

wherein $R_{14}$, $R_{15}$, $R_{16}$, $R_{17}$ and HX have the meanings given in Table 1.

TABLE 1

| | | ANOREXIA ACTIVITY OF SOME COMPOUNDS OF THE INVENTION | | | | |
|---|---|---|---|---|---|---|
| X | $R_{14}$ | $R_{15}$ | $R_{16}$ | $R_{16}$ | %Anorexia | Dose (mg/kg) |
| Cl | phenyl | —CH$_2$N(CH$_3$)$_2$ | CH$_3$ | H | 64 | 20 |

TABLE 1-continued
ANOREXIA ACTIVITY OF SOME COMPOUNDS OF THE INVENTION

| X | R₁₄ | R₁₅ | R₁₆ | R₁₆ | %Anorexia | Dose (mg/kg) |
|---|---|---|---|---|---|---|
| Cl | phenyl | —CH₂N(CH₃)₂ | CH₂C₆H₅ | H | 16 | 25 |
| Cl | phenyl | —CH₂N(CH₃)₂ | H | H | 22 | 40 |
| Br | 3-C₃phenyl | —CH₂N(CH₃)₂ | CH₃ | H | 4 | 25 |
| Br | 4-C₃phenyl | —CH₂N(CH₃)₂ | CH₃ | H | 32 | 20 |
| Br | 2-naphthyl | —CH₂N(CH₃)₂ | CH₃ | H | 76 | 25 |
| Br | 4-Clphenyl | —CH₂N(CH₃)₂ | CH₃ | H | 81 | 24.2 |
| Cl | phenyl | —CH₂NHCH₃ | CH₃ | H | 65 | 20 |
| Br | phenyl (a) | —CH₂N(CH₃)₂ | CH₃ | CH₃ | 41 | 25.4 |
| Br | phenyl (b) | —CH₂N(CH₃)₂ | CH₃ | CH₃ | 14 | 25.4 |
| Br | phenyl | OH<br>\|<br>—CHCH₂N(CH₃)₂ | CH₃ | H | 54 | 26.2 |

(a) = Slower moving isomer on thin layer chromatography (petrol-ether eluant)
(b) = Faster moving isomer on thin layer chromatography (petrol-ether eluant)

The isomer of 7- dimethylaminoethyloxy -2- methyl -4-phenyl - 1,2,3,4 - tetrahydroIsoquinoline dihydrochloride which had a negative rotation gave 65% anorexia at 20 mg/kg whereas the isomer which had a positive rotation gave 13% anorexia at 20 mg/kg.

Thus the preferred isomers of the compounds of the formula (II) for the induction of anorexia are those which have the same stereochemistry as (-) -7- dimethylaminoethyloxy -2- methyl -4- phenyl -1,2,3,4- tetrahydroisoquinoline dihydrochloride.

The useful mood modifying activity of the compounds of this invention may be determined by standard test such as the Reserpine Prevention test which demonstrates the ability of the compounds to prevent reserpine induced hypothermia in mice. The approximate dose in mg/kg at which certain compounds of the formula (VII b) are active on the Reserpine Prevention test in the mouse is given in Table 2:

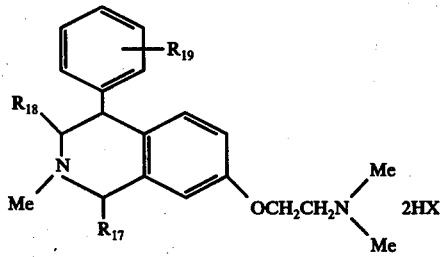

wherein R₁₇, R₁₈, R₁₉ and HX have the meanings given in Table 2.

TABLE 2
MODE AT WHICH CERTAIN COMPOUNDS OF THE INVENTION ARE ACTIVE IN THE RESERPINE PREVENTION TEST IN MICE

| HX | R₁₇ | R₁₈ | R₁₉ | Approximate Dose Required (mg/kg) |
|---|---|---|---|---|
| HCl | H | H | H | 0.03 |
| HCl | H | H | 3-CF₃ | 1 |
| (CHOHCO₂H)₂ | H | Me | H | 1 |
| HBr | H | H | 4-Cl | 0.1 |
| HBr | CH₃(a) | H | H | 0.1 |

1,2,3,4 - tetrahydro -2- methyl -7- (2-dimethylaminoethoxy) -4-phenyl - isoquinoline hydrochloride and 4 - (3-trifluoromethyl phenyl) - 1,2,3,4 - tetrahydro -2- methyl -7- (2 - dimethylaminoethoxy) isoquinoline hydrochloride have approximate oral LD 50's in the mouse of 280 mg/kg and greater than 100 mg/kg respectively.

The present invention also provides processes for the preparation of the compounds of this invention as follows: (a) The compounds of the formula (II) may be prepared from the corresponding compound of the formula (VIII)

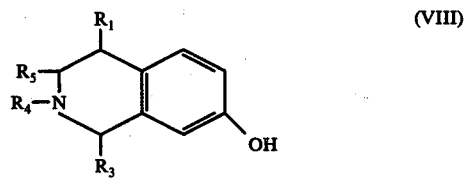

and salts thereof wherein R₁, R₃, R₄ and R₅ are as defined in relation to formula (II) by reaction with an etherifying agent such as that of the formula QR₂ or an acid addition salt thereof wherein R₂ is as defined in relation to formula (II) and Q is a readily displaceable group.

Suitable groups Q are those readily displaced by nucleophilic groups and include the chlorine, bromine and iodine atoms and the hydroxyl group esterified by methane sulphonic, toluene sulphonic or like acid activated ester.

Particularly suitable groups Q include iodine atoms.

The etherification reaction will normally be carried out in an inert solvent. Suitable solvents include hydrocarbons such as toluene or xylene, ethers such as dimethoxyethane or tetrahydrofuran or ketones such as acetone, alcohols such as ethanol and other conventional solvents.

If desired the anion of the compound of formula (VIII) may be produced before the etherification reaction or may be produced in situ by reaction with a base such as NaH or the like.

Generally any non-extreme temperature is used, but the reaction is substantially complete in a conveniently short time if an elevated temperature is used. For example the reaction may be carried out at from about 0° –180° C, preferably in the region of 50° –120° C.

The compounds of formula (VIII) may be prepared by the demethylation of the corresponding compound of the formula (IX):

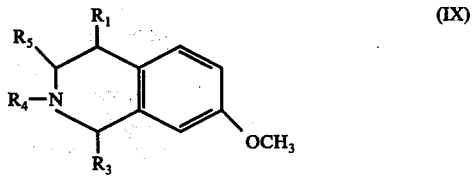

brought about by treatment with a strong acid such as hydrobromic acid.

(b) The compounds of the formula (II) may be prepared by the reaction of an amine R₆R₇NH with a compound of the formula (X):

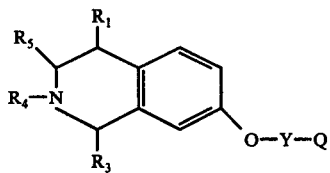

wherein R₁, R₃, R₄, R₅, R₆ and R₇ are as defined in relation to formula (II), Y is a

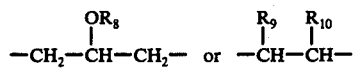

group wherein R₈, R₉ and R₁₀ are as defined with respect to formula (II) and Q is a readily displaceable group or when it is required to form a compound of the formula (II) wherein R₈ is a hydrogen atom Q may be taken together with Y to form a

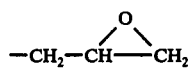

group.

Suitable displaceable groups Q include those as herein before defined.

Such a reaction may take place at any non-extreme temperature for example, 0° C – 180° C, but generally ambient or moderately elevated temperatures, for example 12° C – 100° C are particularly suitable.

The displacement reaction normally takes place in an organic solvent such as ethanol, ether or the like. (c) The compounds of the formula (II) may be prepared by the cyclisation of a compound of the formula (XI):

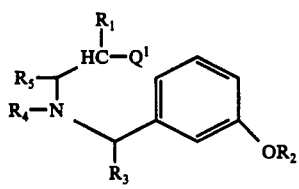

and salts thereof wherein R₁, R₂, R₃, R₄ and R₅ are as defined in relation to formula (II) and Q¹ is a group Q wherein Q is a readily displaceable group as hereinbefore defined.

Suitably Q¹ is a hydroxyl group or a C₁₋₄ acyloxy group.

Such a process may be effected in the presence of an acidic cyclisation agent at a non-extreme temperature in a solvent.

Suitable acidic cyclisation agents are sulphuric acid, phosphoric acid, boron trifluoride, aluminium chloride, tin tetrachloride, etc. Suitably the temperature will be between 10° C and 150° C. (d) The compounds of the formula (II) may be prepared by the reduction of a compound of the formula (XII)

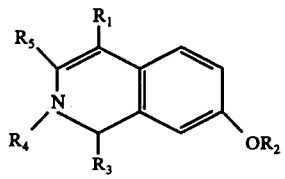

wherein R₁, R₂, R₃, R₄ and R₅ are as defined in relation to formula (II).

Such a reduction may suitably be effected in the presence of a transition metal catalyst and hydrogen or by a complex alkali metal hydride in an organic solvent at a non-extreme temperature.

Suitably the transition metal catalyst is platinum, palladium or rhodium or a derivative thereof. Suitably the reduction is carried out in a lower alkanol at a temperature of −20° C to +100° C.

Suitably the complex metal hydride is sodium borohydride or lithium aluminium hydride. (e) The compounds of the formula (II) may be prepared by the reduction of a compound of the formula (XIII)

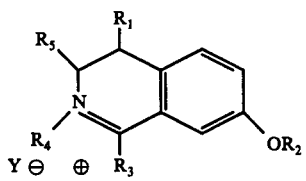

wherein R₁, R₂, R₃, R₄ and R₅ are as defined in relation to formula (II) and Y is an anion of an acid.

Such a reduction may suitably be effected in the presence of a transition metal catalyst and hydrogen or a complex alkali metal hydride in an organic solvent at a non-extreme temperature.

Suitably the transition metal catalyst is platinum, palladium or a derivative thereof and the complex alkali metal hydride is sodium borohydride or lithium aluminium hydride. Suitably the reaction is carried out in a lower alkanol or in the case of lithium aluminium hydride an open chain or cyclic ether.

(f) The compounds of the formula (II) may be prepared by the reduction of a compound of the formula (XIV)

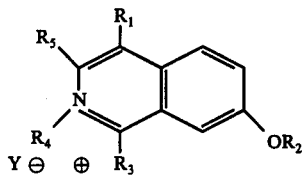

wherein R₁, R₂, R₃, R₄, and R₅ are as defined in relation to formula (II). and Y⁻ is an anion of an acid.

Such a reduction may suitably be effected under the conditions of processes (d) and (e) hereinbefore described. (g) The compounds of the formula (II) wherein R₂ is a group

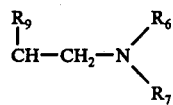

wherein $R_6$, $R_7$, and $R_9$ are as defined in relation to formula (II) may be prepared by the reduction of a compound of the formula (XV)

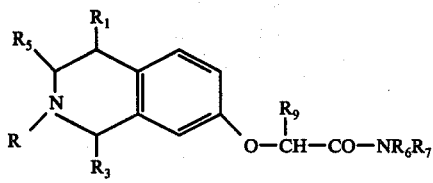 (XV)

wherein $R_1$, $R_2$, $R_3$, $R_4$, $R_5$, $R_6$, $R_7$ and $R_9$ are as defined in relation to formula (II) with a complex metal hydride capable of reducing amides to amines.

Such a reduction may suitably be effected with lithium aluminum hydride in an open-chain or cyclic ether, for example diethylether, tetrahydrofuran, dioxan or the like, at a non-extreme temperature such as −30° C to +100° C. (h) The compounds of the formula (II) wherein $R_7$ is a hydrogen atom may be prepared by the hydrogenation of the corresponding compound of the formula (II) wherein $R_7$ is a group removable by hydrogenolysis. (i) The compounds of the formula (II) wherein $R_6$, $R_7$ and $R_{10}$ are all hydrogen atoms may be prepared by the reduction of a compound of the formula (XVIa) or (XVIb)

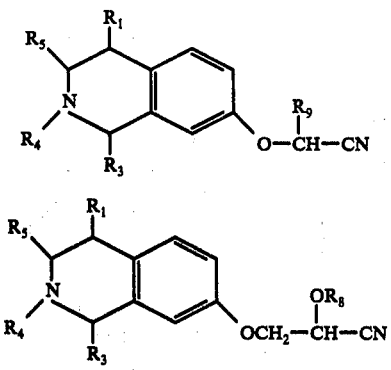

wherein $R_1$, $R_3$, $R_4$, $R_5$, $R_8$ and $R_9$ are as defined in relation to formula (II).

It has been further found that such a reduction may suitably be effected by a complex alkali metal hydride such as lithium aluminium hydride in an ethereal solvent, for example diethyl ether, tetrahydrofuran or dioxan, at a non-extreme temperature, i.e. −30° C to +100° C (j) The compounds of the formula (II) wherein $R_6$ and/or $R_7$ are alkyl groups may be prepared by the alkylation of the corresponding compounds of the formula (II) wherein $R_6$ is a hydrogen atom and $R_7$ is a hydrogen atom or an alkyl group, (k) The compounds of the formula (II) wherein $R_4$ is an alkyl group may be prepared by the alkylation of the corresponding compounds of the formula (II) wherein $R_4$ is a hydrogen atom.

The alkylation process in (j) and (k) as hereinbefore described may be performed by conventional methods of alkylation. Particularly suitable methods of alkylation include reductive alkylation using an aldehyde in the presence of a reducing agent. For example, compounds of the formula (II) wherein $R_4$, $R_6$, and/or $R_7$ are methyl groups may be prepared by reaction with formaldehyde in the presence of formic acid or by reaction with formaldehyde in the presence of a reducing agent such as hydrogen and a transition metal catalyst.

Such reaction normally takes place at a non-extreme temperature such as −10° C to +120° C, for example, 10° C to 60° C and preferably at ambient temperature. Such reaction frequently takes place in a conventional organic solvent.

It will be appreciated that compounds of the formulae (XI), (XII), (XIII) and (XIV) are important novel intermediates and as such form an important aspect of the present invention.

The compounds of the formula (X) may be prepared by: (a) the reduction of a compound of the formula (XVII) or (XVIII):

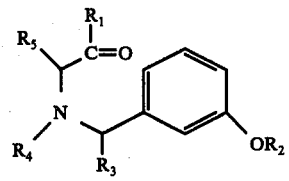 (XVII)

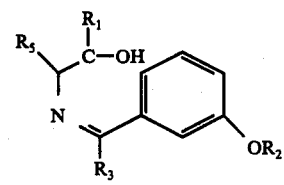 (XVIII)

with a complex metal hydride or (b) heating a compound of the formula

with a compound of the formula (XIX):

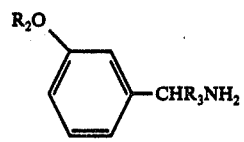 (XIX)

in an inert hydrocarbon; wherein $R_1$, $R_2$, $R_3$, $R_4$ and $R_5$ are as defined with respect to formula (XII).

The compounds of the formula (XII) may be prepared by the reaction of a compound of the formula (XX):

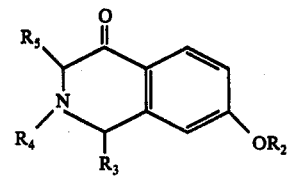 (XX)

wherein $R_2$, $R_3$, $R_4$ and $R_5$ are as defined in relation to formula (XV) and a metal derivative $R_1M$ where M is Li, Na, MgI, MgBr or MgCl in conventional manner followed by dehydration.

The initial step of such reaction takes place in aprotic media, for example, in an ether solvent such as diethylether, tetrahydrofuran, dimethoxyethane or the like. The dehydration stage may conveniently be carried out using an aqueous or alkanolic solution of an acid in conventional manner. The compounds of the formula (XIII) may be prepared by the cyclodehydration of a compound of the formula (XXI).

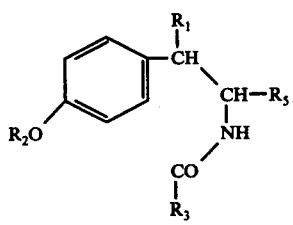

wherein $R_1$, $R_2$, $R_3$, and $R_5$ are as defined in relation to formula (X); followed by the modification of the secondary amine group as required.

Such a cyclisation process will be carried out in the presence of a condensing agent and suitably in the presence of phosphorus pentoxide or zinc chloride.

Certain compounds of the formula (II) can be prepared as their optically active forms by the resolution of a compound of the formula (IX) as hereinbefore defined followed by the transformation of the resolved compound of the formula (IX) into a compound of the formula )II0 (II) the manner described herein.

The compound of the formula (IX) may be resolved by the reaction of a compound of the formula (IX) wherein $R_4$ is a hydrogen atom with an optically active acid, for example, (+)— or (—)— tartaric acid, or (+)— or (—)— dibenzoyl tartaric acid followed by the conversion of the so-formed optically active salt in the optically active form of the compound of the formula (IX) by base.

The reaction of the compound of the formula (IX) with the optically active acid will normally take place in a suitable aqueous or organic solvent, for example a lower alkanol such as methanol or ethanol, at a non-extreme temperature, such as $-10°$ C to $+100°$ C, for example ambient temperature.

The optically active salt will usually be converted into the optically active compound of the formula (IX) by reaction with a solution of an inorganic base, such as carbonate or hydroxide, in water at a non-extreme temperature, for example ambient temperature.

The groups $R_4$, $R_6$, $R_7$ and $R_8$ of the compounds of the formula (II) may be converted into other groups $R_4$, $R_6$, $R_7$ and $R_8$ by conventional methods well known to those skilled in the art.

The following examples are illustrative of the invention.

EXAMPLE 1

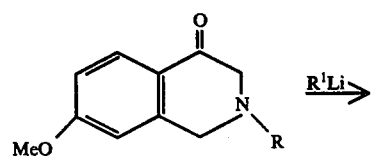

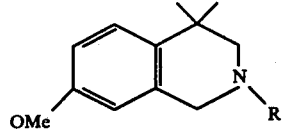

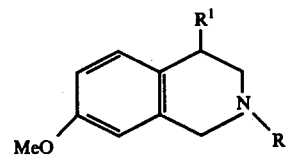

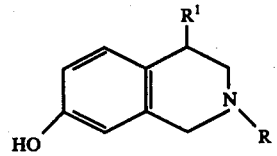

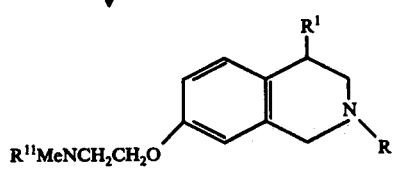

a. Preparation of 2-substituted - 7 - methoxy - 2,3 - dihydro -4(IH) - isoquinolones (1)

Prepared according to the method of G. Grethe, H. C. Lee, M. Uskokvic a A. Brossi: J. Org. Chem. 1968, 33, 491.

b. Preparation of 7-Methoxy -2-Methyl -4-(4-trifluoromethyl phenyl) -1,2,3,4-tetrahydro-4-isoquinolinol (2, R=Me, $R^1$ = 4-CF$_3$Ph)

A solution of (1,R=Me), (6.46g) in dry tetrahydrofuran (50ml.) was added dropwise under nitrogen to a solution of 4-trifluoromethylphenyl-lithium (prepared from 4-bromobenzotrifluoride (15.0g) and n-butyl-lithium (28.5 ml., 2.4N) in dry tetrahydrofuran at $-70°$. After the addition the solution was warmed to room temperature and stirred overnight. Water (50ml) was added dropwise and the tetrahydrofuran removed under reduced pressure. The aqueous layer was extracted with ether and the ether layers combined and dried (MgSO$_4$). Removal of the solvent under reduced pressure gave the title compound which was used without further purification in the next reaction.

Similarly prepared were the compounds (2) wherein:

| R=Me | $R^1$=Phenyl | R=Me | $R^1$=2-Naphthyl |
|---|---|---|---|
| R=Me | $R^1$=4-Phenyl | R=H | $R^1$=Phenyl |

-continued

| R=Me R¹=3-CF₃ Phenyl | R=Benzyl R¹=Phenyl | c. Preparation of 7-Methoxy-2-methyl-4-(4-trifluoromethylphenyl)-1,2,3,4-tetrahydroisoquinoline (3,R=Me. R¹=4CF₃-Phenyl)

The crude oil (2, R=Me, R¹ =4CF₃Ph) obtained from the above reaction was dissolved in saturated ethanolic hydrogen chloride (100ml) and solution refluxed for 2 hr. Ethanol was removed under reduced pressure, the residual oil dissolved in methanol (100 ml) and sodium borohydride (7g) added portionwise. The solution was left to stand for ½ hr. Methanol was removed under reduced pressure and the residue taken up in dichloromethane and water and the aqueous layer extracted with dichloromethane. Removal of the solvent under reduced pressure gave an oil which was taken up in ether and extracted with dilute hydrochloric acid (2N). The aqueous layer was basified (2N,NaOH), extracted with ether and the organic layers dried. Removal of the solvent under reduced pressure gave the title compound.

$\tau(CDCl_3)$: 7.63 (3H,s), 7.55–6.85 (2H,m), 6.35 (2H,s), 6.25 (3H,s), 5.75 (1H,t), 3.5–3.1 (3H,m), 2.75–2.35 (m).

Similarly prepared were (3,R=Me, R¹=Phenyl)$\rho(CDCl_3)$: 7.6 (3H,s), 7.5–6.8 (2H,m), 6.35 (2H,s), 6.25 (3H,s), 5.8 (1H,dd), 3.5–3.1 (3H,m), 2.8 (5H,s). m.p. (as the hydrochloride) 235° – 237°.

(3, R=Me, R¹=4-Cl Phenyl)$\tau(CDCl_3)$: 7.65 (3H,s), 7.5–6.9 (2H,m), 6.4(2H,s) 6.3(3H,s), 5.85 (1H,t,J=6Hz), 3.5–3.1 (3H,m), 3.0–2.6 (4H,m) m.p. as the di-HCl salt 244–6° (MeOH - Et₂O).

(3, R=Me, R¹=3-CF₃Phenyl) $\tau(CDCl_3)$: 7.65 (3H,s), 7.5 – 6.9 (2H,m), 6.4 (2H,s), 6.3 (3H,s) 5.8 1 (1H,t), 3.5–3.2 (3H,m), 2.85–2.3 (4H,m)

(3, R=Me,R¹=2-Naphthyl) $\tau(CDCl_3)$: 7.62 (3H,s) 7.43–6.78 (2H,m) 6.33 (2H,s) 6.28 (3H,s) 5.61 (1H,t) 3.55–3.02 (3H,m), 2.83–1.93 (7H,m)

(3, R=H, R¹=Phenyl) m.p. 212°–14° (EtOH-Et₂O)

(3, Benzyl, R¹ = Phenyl) $\tau(CDCl_3)$: 6.8–7.3 (2H,m), 6.4 (3H,s), 6.3–6.45 (4H, broad s), 5.9 (1H,m), 3.2–3.5(3H,m), 2.9 (5H,s), 2.85 (5H,s).

d. Preparation of 7-Hydroxy -2-methyl -4-(4-trifluoromethyl phenyl)-1,2,3,4-tetrahydroisoquinoline (4,R=Me, R¹=4CF₃ Phenyl)

48% hydrobromic acid (100 ml) was added to (3,R=Me, R¹=4CF₃Ph), (7.0g.) and the solution refluxed for 4.5 hr. and then left to stand at room temperature for 16 hrs. The reaction mixture was poured into water, solid sodium bicarbonate was added until the solution was basic and the solution extracted with dichloromethane. The organic layers were combined and dried (MgSO₄). Removal of the solvent under reduced pressure gave the title compound (5.13g) as a foam.

$\tau(CDCl_3)$: 7.6(3H,s), 7.3–6.8(2H,m), 6.6(2H,s), 5.7 (1H,m), 3.45 (3H,s), 2.85–2.4 (4H,m), 0.9 (1H,s)

Similarly prepared were (4,R=Me, R¹ = Phenyl) $\tau(CDCl_3)$: 7.53 (3H,s), 7.4–6.6(2H,m) 6.3(2H,s), 5.75(1H,m), 3.5(3H,s), 2.9 (5H,s), 1.3(1H,s) m.p. 162°–4° (ether petrol)

(4, R=Me, R¹4—ClPhenyl)$\tau(CDCl_3)$; 7.65 (3H,s), 7.55–6.9 (2H,m), 6.4 (2H,s) 5.9 (1H,m), 3.4(3M,s), 2.85 (4H,s).

(4, R=Me, R¹=3—CF₃Phenyl)$\tau(CDCl_3)$: 7.65 (3H,s), 7.3–6.25 (2H,m), 6.5 (2H,s), 5.7(1H,m) 3.5(3H,s), 2.9–2.5(4H,m), 2.4(1H,s).

(4, R=Me, R¹=2—Naphthyl) $\rho(CDCl_3)$: 7.6 (3H,s), 7.45–6.7(2H,m), 6.5(2H;s), 5.6(1H,m) 3.8–3.2(3H,m), 3.0–2.1 (7H,m), 1.5(1H,s). (4, R=H, R¹=Phenyl) m.p. 220°–224° (dec) (Et₂O - Petrol) (4, R=Benzyl R¹ = Phenyl) $\tau(CDCl_3)$ 6.8–7.3 (2H,m), 6.25 (4H, broads), 5.85 (1H,m), 3.2–36 (3H,m), 2.85 (5H,s) 2.78 (5H,s), 2(broad 1H)

e. Preparation of 7-(Dimethylaminoethyloxy)-2-methyl-4-(4-trifluoromethylphenyl)-1,2,3,4-tetrahydroisoquinoline (5, R=Me, R¹=4—CF₃ Phenyl, R¹¹=Me)

Sodium hydride (0.34 g of an 80% dispersion in oil) was added to (4,R=Me, R¹=4—CF₃Ph), (2.9g) in dry tetrahydrofuran (60 ml). Dimethylaminoethyl chloride (1.1g) and sodium iodide were added and the mixture was refluxed for 48 hrs. The solvent was removed under reduced pressure, the residue dissolved in water and ether and the aqueous layer extracted with ether. The combined organic layers were dried (MgSO₄). Removal of the solvent under reduced pressure gave an oil which was chromatographed on alumina. Elution with chloroform-ether (1:4) gave the title compound as an oil. Treatment with ethereal hydrogen bromide gave the dihydrobromide salt (m.p. 157°–60°, ethanol ether).

$\tau(CDCl_3)$ free base. 7.8(6H,s), 7.75(3H,s), 7.4 (2H,E,J=6Hz), 7.6–6.9(2H,m), 6.5(2H,s), 6.1 (2H,E,J=6Hz), 5.9(1H,E,J=6Hz), 3.5 (3H,s), 2.95–2.55(4H,m).

$\tau(DMSO)$ 2HBrsalt: 7.07 (6H,s), 7.0 (3H,s), 6.6–6.05(4H,m), 6.0–5.0 (5H,m), 3.5–3.0 (3H,m), 3.0–2.5 (4H,m). Found: C: 46.56, H; 5.00, N; 4.73, $C_{21}H_{27}Br_2F_3N_2O$ requires: C; 46.68, H; 5.04, N; 5.19% Similarly prepared were:

(5,R=Me, R¹ = Phenyl, R¹¹=Me)

$\tau(CDCl_3)$ free base: 7.72 (6H,s), 7.65 (3H,s), 7.35 (2H,t J=6Hz), 6.8–7.7 (2H,m), 6.4 (2H broad s), 5.03 (2H,t, J=6Hz), 5.85(1H,m), 3.2–3.5 (3H,m), 2.88 (5H,s). m.p. 2HCl salt 200° (dec) (EtOH - EtOAc)

(5, R=Me, R¹=4—ClPh, R¹¹=Me)

$\tau(DMSO)$ 2HBr salt: 7.15 (6H,s), 7.0 (3H,s), 6.8–6.1 (5H,m), 5.8–5.2 (4H,m), 3.5–2.9 (3H,m), 2.9–2.4 (4H,m), 0.5–0.5 (2H, broads) m.p. 173°–176° (ethanol-ether).

(5, R=Me, R¹=3—CF₃Phenyl, R¹¹=Me)

$\tau(CDCl_3)$ free base: 7.7 (6H,s), 7.67(3H,s), 7.35(2H,t J=6Hz), 7.6–6.9 (2H,m), 6.4 (2H,s), 6.0 (2H,t,J=6Hz), 5.8 (1H,t,J=6Hz), 3.4 (3H,s), 2.9–2.4 (4H,m). $\tau(DMSO)$ 2HBr salt: 7.15(6H,s), 7.05 (3H,s), 6.8–6.1 (4H,m), 5.8–5.2 (5H,m), 3.6–3.0 (3H,m), 2.9 (4H,s), 0.5–1.0 (2H, broad D₂O replaceable) m.p. 195°–199° (ethanol-ether).

(5, R=Me, R¹ = 2—naphthyl, R¹¹=Me)

$\tau(CDCl_3)$ free base: 7.8(6H,s), 7.7 (3H,s), 7.3(2H,t,J=6Hz), 7.6–6.9 (2H,m), 6.4(2H,s), 6.05 (2H,t,J=6Hz), 5.7(1H,t), 3.6–3.1(3H,m), 3.0–2.1 (7H,m).

Dihydrobromide salt m.p. 172°–175° (ethanol-ether).

(5,R=H, R¹=Phenyl, R¹¹=Me)

$\tau(CDCl_3)$ free base: 7.7 (6H,s), 7.3(2H,t,J=Hz), 6.6–7.1 (2H,m), 5.8–6.1 (5H,m), 4.9(1H broad s, exch D₂O), 3.3-3.45 (3H,m) 2.7-3.0 (5H,m). m.p. (dihydrochloride) 200° (dec) (EtOH-EtOAc)

(5, R=Benzyl, R¹=Phenyl, R¹¹=Me)

τ(CDCl₃) free base 7.70 (6H,s), 7.32 (2H,t,J=6Hz), 6.8-7.3 (2H,m), 6.36 (2H, broad s), 6.3 (2H broad s) 6.0 (2H,t, J=Hz), 5.95 (1H,m), 3.3-3.5 (3H,m), 2.8(5H,s), 2.75(5H,s). m.p. (dihydrochloride monohydrate) 192°-194° (EtOH-EtOAC).

(5, R=Me, R¹=Phenyl, R¹¹ = Benzyl)

τ(CDCl₃) free base: 7.7 (3H,s), 7.65 (3H,s), 7.2 (2H,t,J=6H), 7.4-6.9 (2H,m), 6.4 (4H,s+s), 6.0 (2H,t,J=6H), 5.9 (1H,m), 3.5-3.2 (3H,m), 2.8 (5H,s), 2.7 (5H,s).

Preparation of 2-Methyl(-7-(Methylaminoethoxy)-4-phenyl-1,2,3,4-tetrahydroisoquinoline (5, R=Me, R¹ = Phenyl, R¹¹=H.

The above compound (5, R=Me, R¹=Phenyl, R¹¹ = Benzyl) was hydrogenated at 50° C and 65 p.s.i. in ethanol in the presence of Raney nickel to give the title compound.

(DMSO) dihydrochloride: 7.4 (3H,s), 7.2 (3H,s) 6.9-6.1 (4H,m), 5.9-5.2 (5H,m), 3.5-3.0 (3H,s), 2.6 (5H,s), 0.5 (2H, broad). m.p. 188°-192° (EtOH).

EXAMPLE 2

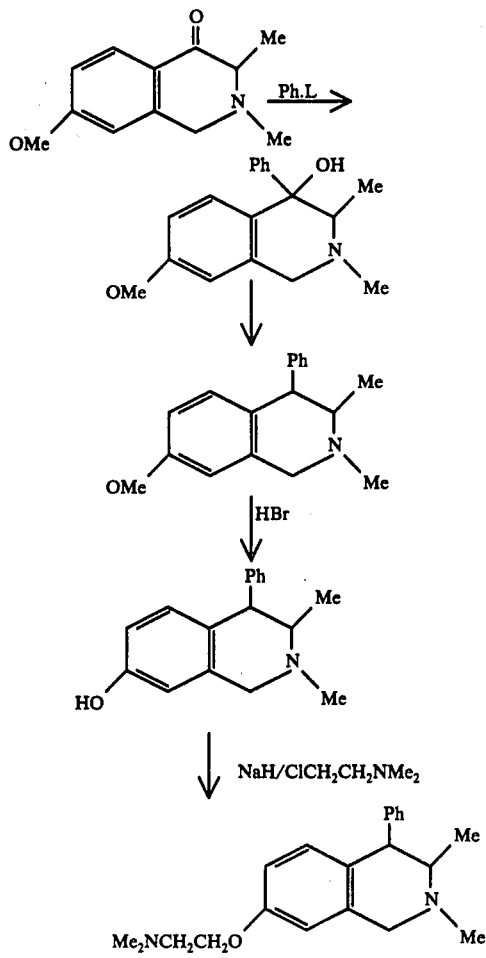

a. 2,3- Dimethyl -7-methoxy -2,3-dihydrol -4-(1H)-Isoquinolone (6) was prepared according to G. Grete et al J. Org Chem 1968, 33, 491.

b. Preparation of 2,3-Dimethyl-7-methoxy-4-phenyl-1,2,3,4 -tetrahydro--4-isoquinolinol (7).

Phenyl-lithium (126 ml, 2N) was added dropwise under nitrogen to a solution of (6) (21g) in dry tetrahydrofuran (200 ml) at 70°. The solution was warmed to room temperature and left to stir for 1 hr. Water (50ml) was added and the tetrahydrofuran was removed under reduced pressure. The residue was extracted with ether and the combined ether layers dried (MgSO₄). Removal of the solvent under reduced pressure gave the title compound.

c. Preparation of 2,3-Dimethyl -7-methoxy-4-phenyl-1,2,3,4-tetrahydroisoquinoline (8)

Saturated ethanolic hydrogen chloride (800 ml) was added to (7) (21 g) and the solution was refluxed for 2 hr. and left to stand at room temperature for 16 hr. Ethanol was removed under reduced pressure, the residue was taken up in methanol and sodium borohydride (30 g) added portion-wise. Methanol was removed under reduced pressure and the residue taken up in water and ether. The aqueous layer was extracted with ether and the combined ether layers extracted with dilute sulphuric acid(2N). The acid layers were basified and extracted with ether. The combined ether layers were dried (MgSO₄). Removal of the solvent under reduced pressure gave the title compound as an oil.

τ (CDCl₃):9.15 (3H, d, J=6Hz), 7.6 (3H,s), 7.1 (1H,dq), 6.2(3H,s), 6.1(2H,s), 5.9 (1H,d,J=6Hz), 3.4-3.0 (3H,m), 2.7(5H,s).

d. Preparation of 2,3-dimethyl-7-hydroxy-4-phenyl-1,2,3,4-tetrahydroisoquinoline (9).

Hydrobromic acid (100 ml) was added to (8) 8.5 g and the solution refluxed for 2 hr. and left to stand at room temperature overnight. The reaction mixture was poured into water and soidum bicarbonate added until the solution was basic. The solution was extracted with chloroform and the combined organic layers dried. (MgSO₄). Removal of the solvent under reduced pressure gave the title compound as a foam in quantitative yield.

τ(CDCl₃): 9.1 (3H,d,J=6Hz), 7.3 5 (3H,s), 6.7 (1H,m), 6.1 (2H,s), 5.4 (1H,d,J=6Hz), 3.3(3H,s), 2.85(5H,s), 1.35 (1H, broad).

e. Preparation of 2,3-dimethyl-7-dimethylaminoethyloxy-4-phenyl-1,2,3,4-tetrahydroisoquinoline (10)

Sodium hydride (0.5g) was added to a solution of (9) (5g) in dry tetrahydrofuran (100ml) and the mixture left to stir for ½ hr. Dimethylaminoethyl chloride (3.22 g) and sodium iodide (0.05g) were added and the mixture was refluxed for 48 hr. The solvent was removed under reduced pressure and the residue taken up in water and ether. The aqueous layer was extracted with ether and the ether layers dried. (MgSO₄). Removal of the solvent under reduced pressure gave an oil which was chromatographed on alumina. Elution with 1:1 chloroform ether gave the title compound (2.1g) as an oil. The oil was taken up in butan-2-one and treated with a stoichiometric amount of d-tartaric acid. The precipitated ditartrate salt (mp 88°-92°) was collected and heated at 60° at 0.2 mm for 20 hr for complete removal of butan-2-one.

τ(CDCl₃) free base: 9.2 (3H,d,J=6Hz), 7.7 (6H,s), 7.65 (3H,s), 7.35 (2H,t,J=6Hz), 7.35(1H,m), 6.3 (2H,m), 6.0 (2H,t,J=6Hz), 6.0 (1H,d,J=6Hz) 3.5 3.1 (3H,m), 2.85 (5H,s).

τ(DMSO) ditartrate:9.2 (3H,d,J=6Hz), 7.55 (3H,s), 7.3(6H,s), 7.35 (1H,m), 6.7(2H,m), 6.0 (2H,m), 5.8 (7H,s), 3.2 (3H,s), 2.8 (5H,s), 2.3 (8H,s, disappears with D₂O).

EXAMPLE 3

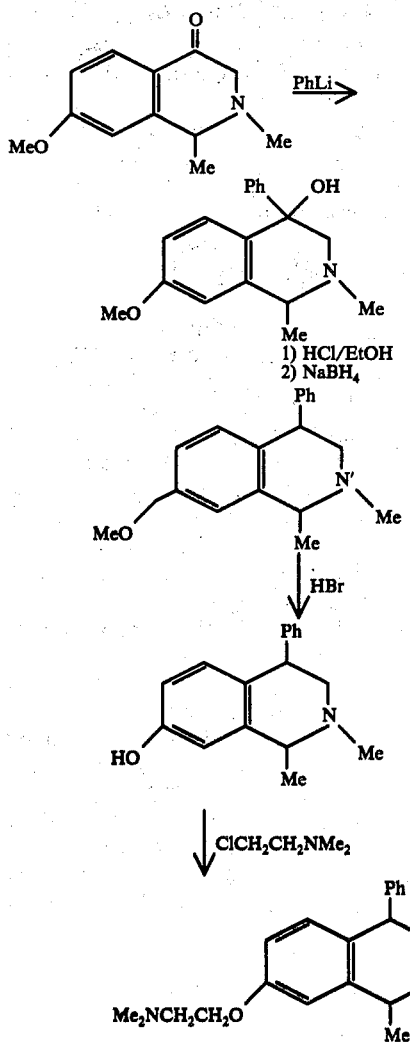

a. 1,2-Dimethyl-7-methoxy-2,3-dihydro-4-isoquinolone (11) was prepared according to J. Org Chem. 1968, 33, 491.

b. 1,2-Dimethyl-7-methoxy-4-phenyl-1,2,3,4-tetrahydro-4-isoquinolinol (12) was prepared in an identical manner to that of the 3-methyl analogue (7). The nmr spectrum (CDCl₃) revealed an ~3:2 ratio of racemic disastereoisomers, as shown by two distinct N-methyl resonances at τ7.72 and τ7.68.

c. 1,2-Dimethyl-7-methoxy-4-phenyl-1,2,3,4-tetrahydroisoquinoline (13) was prepared in an identical manner to that of the 3-methyl analogue (8). The final oil (21g) was chromotographed twice on alumina (60:1 ratio, eluting with petrol-ether (1:5) to ether) to give 3.7 g of one racemic disastereoisomer (higher R_f). τ(CDCl₃) 8.57(3H,d,J=6Hz), 7.61 (3H,s), 7.45-6.65(2H,m), 6.4(1H,q,J=6Hz). 6.3 (3H,s), 5.82 (1H,dd,), 3.45-3.15 (3H,m), 2.85 (5H,m).

Continued elution gave mixtures of diastereoisomers leading to the pure lower R_f racemic diastereoisomer (6.9g). τ(CDCl₃): 8.55 (3H,d,J=6Hz), 7.45 (3H,s), 7.3-6.7 (2H,m), 6.28(3H,s + 1H,q), 5.85 (1H,t,J=6Hz), 3.45-3.1 (3H,m), 2.9-2.5 (5H,m).

d. 1,2-Dimethyl-7-hydroxy-4-phenyl-1,2,3,4-tetrahydro isoquinoline (14)

The higher R_f racemic diastereoisomer (τ (CDCl₃): 8.6 (3H,d,J=6Hz), 7.55 (3H,s), 7.45 - 6.65 (2H,m), 6.38(1H, q,J=6Hz) 5.84 (1H, dd), 3.4 (3H,s), 2.8 (5H,s) was prepared in 66% yield from the higher R_f 7-methoxy racemic diastereoisomer in an identical manner to that of the 3-methyl analogue (9).

Likewise the lower R_f racemic diastereoisomer was prepared in 88% yield. τ (CDCl₃): 8.61 (3H,d,J=6Hz), 7.54 (3H,s), 7.3-7.7 (2H,m), 6.21 (1H,q,J=6Hz), 5.8 (1H,t,J=6Hz), 3.55 (1H,s), 3.39 (2H,s), 3.02 (1H,s), 2.77 (5H,s).

e. 1,2 Dimethyl-7-dimethylaminoethyloxy-4-phenyl-1,2,3,4-tetrahydro isoquinolinol (15)

Both racemic diastereoisomers were prepared separately from the individual phenol precursors using sodium hydride and dimethylaminoethyl chloride by the method used to make compound (10).

Lower R_f racemic diastereoisomer Free base τ (CDCl₃): 8.55 (3H,d,J=6H₂), 7.7 (6H,s), 7.55 (3H,s), 7.3 (3H,t,J=6Hz), 7.05 (2H,m), 6.25 (1H,q,J=6Hz), 5.98 (2H,t,J=6Hz), 5.85 (1H,t,J=6Hz), 3.3 (3H,s), 2.8 (5H,s), 2HBr salt τ (DMSO): 8.45 (3H,d,J=6Hz), 7.4 (3H,s), 7.2 (6H,s), 6.84 (2H,m), 6.58 (2H,t J=6Hz), 5.95-5.45 (4H,m), 3.2 (2H,s), 3.05 (1H,s), 2.72 (5H,s).

Higher R_f racemic diastereoisomer Free base τ (CDCl₃): 8.55 (3H,d,J=6Hz), 7.7 (6H,s), 7.6 (3H,s), 7.35 (2H,t,J=6Hz), 7.5 - 6.75 (2H,m), 6.4 (1H,q, J=6Hz), 6.0 (2H,t,J=6Hz), 5.8 (1H,t,J=6Hz), 3.4–3.1 (3H,m), 2.8 (5H,s).

2HBr salt τ (DMSO): 8.26 (3H,d,J=6Hz), 7.15 (9H, broad s) 6.9 - 6.1 (4H,m), 5.9 - 5.0 (4H,m), 3.9 - 2.9 (3H,m), 2.7 (5H,s), 0.5 - 1.0 (2H, broad).

EXAMPLE 4

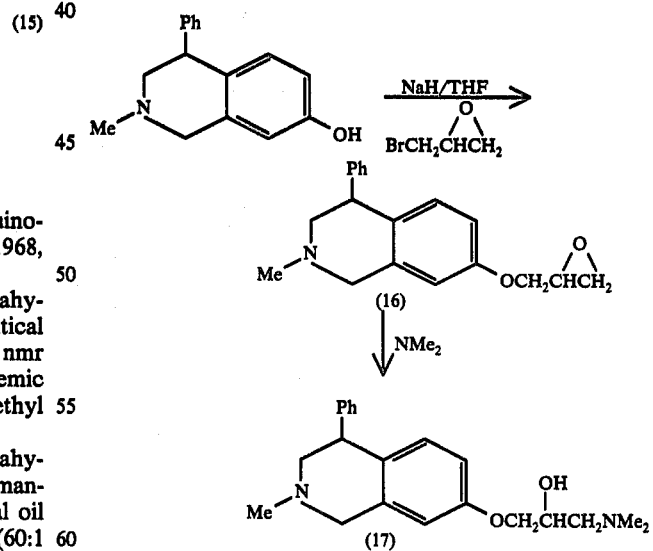

a. Preparation of 7-(2,3-Epoxypropyloxy)-2-methyl-4-phenyl-1,2,3,4-tetrahydroisoquinoline (16)

Sodium hydride (0.72g) was added to a solution of 7-hydroxy-2-methyl-4-phenyl-1,2,3,4-tetrahydroisoquinoline (2.33g) in dry tetrahydrofuran (75 ml). Epibromohydrin (4.11 g) was added and the solution refluxed for 2 hr. until thin layer chromatography (alumina, chloroform-ether 1:5) showed the absence of starting phenol. Water (25ml) was added and the mixture extracted with ether. The combined ether layers were dried (MgSO$_4$) and the solvent removed under reduced pressure. The oil was taken up in xylene (50 ml) and evaporated to dryness to give the title compound in quantitative yield. $\tau$ (CDCl$_3$) 7.68 (3H,s), 7.55–7.0 (3H,m), 6.95–6.6 (2H,m), 6.4 (2H,s), 6.2–5.65 (3H,m), 3.5–3.1 (3H,m), 2.85 (5H,s).

b. Preparation of 7-(3-Dimethylamino-2-hydroxypropyloxy)-2-methyl-4-phenyl-1,2,3,4-tetrahydroisoquinoline (17)

Excess dimethylamine in ethanol was added to a solution of the epoxide (16) in ethanol and the solution allowed to stand at room temperature for 2 hr. The solvent was removed under reduced pressure. Xylene was added to the residue and the solvent evaporated. This procedure was repeated twice to yield a clear oil.

$\tau$ (CDCl$_3$): 7.77 (6H,s), 7.68 (3H,s), 7.59–6.89 (4H,m), 6.42 (2H,s), 6.29–5.59 (5H,m), 3.59–3.19 (3H,m), 2.89 (5H,m), Treatment of the oil with ethereal hydrogen bromide yielded the title compound as the dihydrobromide salt m.p. 77°–82°. $\tau$ (DMSO): 7.4 (3H,s), 7.15 (6H,s), 6.95–6.5 (4H,m), 6.3–5.4 (7H,m), 3.25 (3H,s), 2.75 (5H,s).

EXAMPLE 5 a. Preparation of (+)-7-methoxy-4-phenyl-1,2,3,4-tetrahydro isoquinoline

The racemic tetrahydroisoquinoline,7-methoxy-4-phenyl-1,2,3,4-tetrahydro isoquinoline,(93 g) was dissolved in absolute ethanol (40 ml) and the solution added to a solution of (−) dibenzoyltartaric acid monohydrate (15.1 g) in absolute ethanol (40 ml). The compound which crystallised during 16 hours was filtered, washed with a little ethanol (ca 5–10 ml) and then with dry ether to give 9.33 g of a white crystalline solid m.p. 153°–6° $[\alpha]_D^{25}$ −79.7° (MeOH). A second crop of 4.45 g was obtained but not further used. Recrystallisation of 9.00 g of the first crop from methanol (100ml) gave 6.56 g of white needles m.p. 161°–5°, $[\alpha]_D^{25}$ −77.7° (MeOH) (rotation unchanged on further recrystallisation).

The salt was suspended in water (200 ml), 2N NaOH added to pH 10 and the suspension extracted with ether. The ether was washed (H$_2$O, saturated NaCl) dried and evaporated to give a pale yellow oil (2.60 g). 100 mg of the compound was dissolved in dry ether and the hydrochloride prepared with ethereal HCl. The white crystalline salt was filtered, washed with ether and dried wt. 105 mg. m.p. 231°–3° C, $[\alpha]_D^{25}$ + 23.0° (H$_2$O).

b. Preparation of (−)-7-methoxy-4-phenyl-1,2,3,4-tetrahydroisoquinoline The mother liquors obtained after the first two crops of the (+) - isomer were filtered off were combined and evaporated and the free base regenerated in the manner described for the (+) isomer, wt. 3.40 g. A solution of 2.8 g of this in ethanol (12 ml) was added to a solution of (+) dibenzoyltartaric acid monohydrate (4.31 g) in ethanol (12 ml).

After 1 hr the pale pink salt was filtered, washed with a little ethanol (~5 ml), dry ether and dried, wt. 5.05 g.m.p. 161°–2°. Crystallisation from methanol (50 ml) gave white needles, 3.45 g, m.p. 164°–5°, $[\alpha]_D^{25}$ + 80.5° (MeOH) (rotation unchanged on further recrystallisation). The free base was regenerated as described for the (+) isomer to give 1.30 g of a pale yellow oil. 100 mg was converted to the white crystalline hydrochloride wt 105 mg, m.p. 231°–3° C, $[\alpha]_D^{25}$ − 20.5° (H$_2$O).

c. Preparation of (+)-7-methoxy-2-methyl-4-phenyl-1,2,3,4-tetrahydro isoquinoline (+)-7-methoxy-4-phenyl-1,2,3,4 tetrahydroisoquinoline (2.4 g) was dissolved in methanol (50 ml) and 35% formaldehyde solution (3 ml) was added. The solution was stirred at ambient temperature for two hours when Raney nickel (1 g) was added and the solution hydrogenated at Atmospheric Pressure. The catalyst was removed by filtration, washed with ethanol and the filtrate and washings evaporated under reduced pressure to give the title compound as a colourless oil. Treatment of the title compound with ethereal hydrogen chloride gave its hydrochloride salt (2.3 g), m.p. 242° − 3° C (dec) (methanol-ether) $[\alpha]_D^{25}$ + 21.8° (water).

d. Preparation of (−)-7-methoxy-2-methyl-4-phenyl-1,2,3,4-tetrahydro isoquinoline This compound was prepared by an analogous method to the (+-isomer. m.p. 241°–2° C (dec) (methanol-ether) $[\alpha]_D^{25}$ − 20.0° (water).

e. Preparation of (+)-7-dimethylaminoethoxy-2-methyl-4-phenyl-1,2,3,4-tetrahydro isoquinoline The title compound was prepared from (+)-7-methoxy-2-methyl-4-phenyl-1,2,3,4-terahydro isoquinoline via (+)-7-hydroxy-2-methyl-4-phenyl-1,2,3,4-tetrahydro isoquinoline which was characterised as its hydrochloride salt m.p. 222°–3° C (methanol-ether) $[\alpha]_D^{25}$ + 24.1° (water) by the method of Example 1. The title compound was characterised as its dihydrochloride salt m.p. 160°–4° (hydroscopic) (ethanol ethyl acetate), $[\alpha]_D^5$ + 13° (water). -tetrahydro f. Preparation of (−)-7-dimethylaminoethoxy-2-methyl-4-phenyl-1,2,3,4-tetrahydro isoquinoline By a strictly analogous method to the (+)-isomers (−)-7-hydroxy-2-methyl-4-phenyl-1,2,3,4-tetrahydro isoquinoline hydrochloride salt, m.p. 222°–3° (dec) (methanol-ether) $[\alpha]_D^{25}$ − 25.6° (water) and (−)-7-dimethylaminoethoxy-2-methyl-4-phenyl-1,2,3,4-tetrahydro isoquinoline dihydrochloride salt, m.p. 160°–5° C (hydroscopic) (ethanol-ethyl acetate), $[\alpha]_D^{25}$ −17° (water) were prepared.

We claim:

1. A compound of the formula (II):

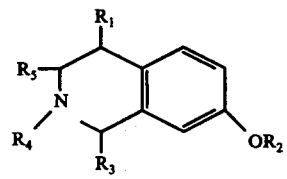

or a pharmaceutically acceptable salt or optically active isomer thereof, wherein R$_1$ is phenyl or naphthyl, or phenyl or naphthyl each substituted by one or two halogen atoms, trifluoromethyl, C$_{1-4}$ alkyl, hydroxy, C$_{1-4}$ alkoxy, nitro, amino, methylamino, dimethylamino, diethylamino, carboxy, methoxycarbonyl, ethoxycarbonyl, cyano, carboxamido, sulphonamido, trifluoromethoxy, trifluoromethylthio or acyl of 2 to 7 carbon atoms; R$_2$ is a group:

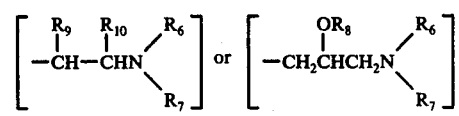

-continued

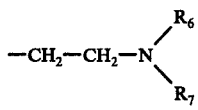 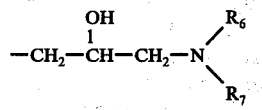

in which $R_6$ is a hydrogen or methyl, $R_7$ is hydrogen or methyl, ethyl or benzyl; $R_3$ is hydrogen or $C_{1-6}$ alkyl or trifluoromethyl; $R_4$ is hydrogen or $C_{1-6}$ alkyl, benzyl or phenyl or acyl of from 2 to 7 carbon atoms; and $R_5$ is hydrogen or $C_{1-6}$ alkyl.

2. A compound according to claim 1 wherein $R_1$ is a phenyl or naphthyl group or a phenyl group substituted by a fluorine, chlorine or bromine atom or a methyl, methoxy or trifluoromethyl group.

3. A compound according to claim 1 wherein $R_2$ is a group of the sub-formula (a), (b), (c) or (d):

$$-CH_2-CH_2-N\begin{matrix}CH_3\\CH_3\end{matrix} \quad (a)$$

$$-CH_2-CH_2NH-CH_3 \quad (b)$$

$$-CH_2-CHOH-CH_2-N\begin{matrix}CH_3\\CH_3\end{matrix} \quad (c)$$

$$-CH_2-CHOH-CH_2-NH-CH_3 \quad (d)$$

4. A compound according to claim 1 wherein $R_3$ is a hydrogen atom.

5. A compound according to claim 1 wherein $R_4$ is a methyl group.

6. A compound according to claim 1 wherein $R_5$ is a hydrogen atom.

7. A compound of the formula (III):

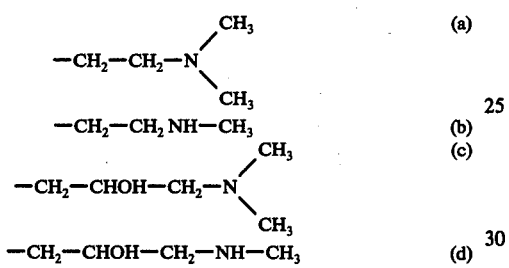

(III)

and pharmaceutically acceptable salts thereof wherein $R_{11}$ is a hydrogen, fluorine or chlorine atom or a nitro, trifluoromethyl methyl or methoxy group and $R_{12}$ and $R_{13}$ are each a hydrogen atom or a methyl or ethyl group.

8. A compound according to claim 7 wherein $R_{11}$ is a 4-fluorine or 4-chlorine atom or a 4-trifluoromethyl group.

9. A compound according to claim 7 wherein $R_{11}$ is a 3-trifluoromethyl group.

10. A compound according to claim 7 wherein $R_{12}$ and $R_{13}$ are each methyl groups.

11. A compound of the formula (IV):

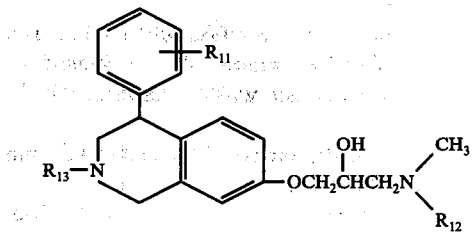

(IV)

and pharmaceutically acceptable salts thereof wherein $R_{11}$ is a hydrogen, fluorine or chlorine atom or a nitro, trifluoromethyl or methoxy group and $R_{12}$ and $R_{13}$ are each a hydrogen atom or a methyl or ethyl group.

12. A compound according to claim 11 wherein $R_{11}$ is a 4-fluorine or 4-chlorine atom or a 4-trifluoromethyl group.

13. A compound according to claim 11 wherein $R_{11}$ is a 3-trifluoromethyl group.

14. A compound according to claim 11 wherein $R_{12}$ and $R_{13}$ are each methyl groups.

15. A compound of the formula (V):

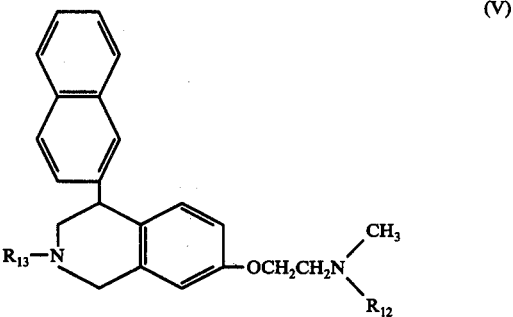

(V)

and pharmaceutically acceptable salts thereof wherein $R_{12}$ and $R_{13}$ are each a hydrogen atom or a methyl or ethyl group.

16. A compound according to claim 15 wherein $R_{12}$ and $R_{13}$ are each methyl.

17. A compound of the formula (VI):

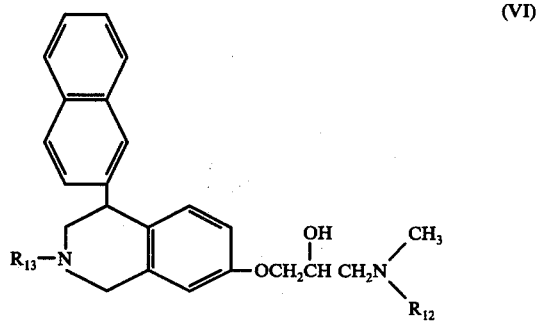

(VI)

and pharmaceutically acceptable salts thereof wherein $R_{12}$ and $R_{13}$ are each a hydrogen atom or a methyl or ethyl group.

18. A compound according to claim 17 wherein $R_{12}$ and $R_{13}$ are each methyl.

19. A compound according to claim 1 in the form of an acid addition salt.

20. A pharmaceutical composition which comprises an anti-depressantly effective amount of a compound as claimed in claim 1 together with a pharmaceutically acceptable carrier.

21. A pharmaceutical composition which comprises an anorexically effective amount of a compound as claimed in claim 1 together with a pharmaceutically acceptable carrier.

22. A pharmaceutical composition according to claim 20 adapted for oral administration to humans.

23. A pharmaceutical composition according to claim 21 adapted for oral administration to humans.

24. An anorexia inducing pharmaceutical composition according to claim 23 containing from 0.5 mg. to 50 mg. of active compound.

25. A mood modifying pharmaceutical composition according to claim 22 containing from 0.05 mg. to 50 mg. of active compound.

26. A method of reducing depression which comprises administering to a depressed human an anti-depressantly effective amount of a compound according to claim 1.

27. A method of reducing appetite which comprises administering to a human an anorexically effective amount of a compound according to claim 1.

28. The compound 7-(dimethylaminoethyloxy)-2-methyl-4-(4-trifluoromethylphenyl)-1,2,3,4-tetrahydroisoquinoline.

29. The compound 2-methyl(-7-(methylaminoethyloxy)-4-phenyl-1,2,3,4-tetrahydroisoquinoline.

30. The compound 2,3-dimethyl-7-dimethylaminoethyloxy-4-phenyl-1,2,3,4-tetrahydroisoquinoline.

31. The compound 7-(3-dimethylamino-2-hydroxypropyloxy)-2-methyl-4-phenyl-1,2,3,4-tetrahydroisoquinoline.

32. The compound (+)-7-dimethylaminoethoxy-2-methyl-4-phenyl-1,2,3,4-tetrahydroisoquinoline.

33. The compound (−)-7-dimethylaminoethoxy-2-methyl-4-phenyl-1,2,3,4-tetrahydroisoquinoline.

* * * * *

UNITED STATES PATENT AND TRADEMARK OFFICE
CERTIFICATE OF CORRECTION

PATENT NO. : 4,113,869
DATED : September 12, 1978
INVENTOR(S) : DEREK VICTOR GARDNER It is certified that error appears in the above-identified patent and that said Letters Patent are hereby corrected as shown below:

In Claim 1: column 20, line 65 delete the two formulae and the brackets enclosing them;

Insert the remaining word "or" between the two formulae at the top of column 21, line 5, so that that line will read:

Signed and Sealed this

Twentieth Day of February 1979

[SEAL]

Attest:

RUTH C. MASON
Attesting Officer

DONALD W. BANNER
Commissioner of Patents and Trademarks